United States Patent
Kitamura et al.

(10) Patent No.: US 10,945,927 B2
(45) Date of Patent: Mar. 16, 2021

(54) PHOSPHATE-BASED DENTAL INVESTMENT MATERIAL

(71) Applicant: SHOFU INC., Kyoto (JP)

(72) Inventors: Toshio Kitamura, Kyoto (JP); Masahiro Kazama, Kyoto (JP)

(73) Assignee: SHOFU INC., Kyoto (JP)

( * ) Notice: Subject to any disclaimer, the term of this patent is extended or adjusted under 35 U.S.C. 154(b) by 134 days.

(21) Appl. No.: 15/981,980

(22) Filed: May 17, 2018

(65) Prior Publication Data

US 2018/0333337 A1 Nov. 22, 2018

(30) Foreign Application Priority Data

May 17, 2017 (JP) .............................. JP2017-097831

(51) Int. Cl.
| | |
|---|---|
| *C09K 3/00* | (2006.01) |
| *A61K 6/838* | (2020.01) |
| *A61C 13/20* | (2006.01) |
| *A61K 6/807* | (2020.01) |
| *A61K 6/827* | (2020.01) |
| *A61K 6/871* | (2020.01) |

(52) U.S. Cl.
CPC .............. *A61K 6/838* (2020.01); *A61C 13/20* (2013.01); *A61K 6/807* (2020.01); *A61K 6/827* (2020.01); *A61K 6/871* (2020.01)

(58) Field of Classification Search
USPC ......................................................... 106/35
See application file for complete search history.

(56) References Cited

U.S. PATENT DOCUMENTS

| | | | | |
|---|---|---|---|---|
| 3,617,315 A | * | 11/1971 | Vickery .................. | A61K 6/90 106/38.3 |
| 3,973,970 A | * | 8/1976 | Mabie ................. | C04B 35/6316 106/35 |
| 6,593,408 B1 | * | 7/2003 | Takaki ..................... | A61K 8/11 524/414 |
| 2007/0283850 A1 | | 12/2007 | Kubo et al. | |
| 2014/0083326 A1 | * | 3/2014 | Mori ........................ | A61K 6/76 106/35 |
| 2015/0136350 A1 | | 5/2015 | Mamada et al. | |
| 2017/0304034 A1 | | 10/2017 | Mori et al. | |

FOREIGN PATENT DOCUMENTS

| | | |
|---|---|---|
| JP | 2003-034608 | 2/2003 |
| JP | 2003-220446 | 8/2003 |
| WO | 2016/084585 | 6/2016 |
| WO | 2016/117395 | 7/2016 |

OTHER PUBLICATIONS

Extended European Search Report dated Nov. 7, 2018, in the corresponding European Patent Application No. 18172552.4.
Grace, "Ludox® Colloidal Silica in Catalyst Applications", Jan. 1, 2015, XP055519239, pp. 1-8.

* cited by examiner

*Primary Examiner* — James E McDonough
(74) *Attorney, Agent, or Firm* — Wenderoth, Lind & Ponack, L.L.P.

(57) ABSTRACT

To provide a phosphate-based dental investment material which can used for metal and press ceramic and especially can impart the lubricity to the surface of a press ceramic, and a phosphate-based dental investment material which can be subjected to a flash heating for press ceramic, can obtain sufficient the hardening expansion, and can easily remove the investment material after press molding. A phosphate-based dental investment material of the present disclosure comprising a powder material and a liquid material, wherein the powder material contains (a) magnesium oxide: 5 to 20 wt. %; (b) ammonium dihydrogenphosphate: 8 to 25 wt. % and the liquid material contains (c) aqueous solution including a cation-treated colloidal silica.

7 Claims, No Drawings

PHOSPHATE-BASED DENTAL INVESTMENT MATERIAL

CROSS-REFERENCE TO RELATED APPLICATIONS

This application is based on and claims the benefit of priority from Japanese Patent Application Serial No. 2017-097831 (filed on May 17, 2017), the contents of which are hereby incorporated by reference in their entirety.

BACKGROUND OF THE INVENTION

Field of the Invention

The present disclosure relates to a phosphate-based investment material used in the dental field.

Description of the Related Art

In a dental prosthetic restoration of a missing part, a lost-wax method has been mainly used in an indirectly preparation method of a dental prosthesis device which is made from metal or ceramic. A description of this method is as follows.

A missing part die having a shape of a dental missing part is prepared by using a die material called as impression material, and a model representing the shape of the dental missing part of a patient outside an oral cavity is prepared by injecting a pattern material such as plaster into the missing part die. Then, a wax is used with the model to represent a shape which should be restored. This is injected in a die material called as investment material. After curing, the wax is incinerated and then replaced by a dental metal or a dental ceramic. A gold alloy for dental use, a gold-silver-palladium alloy for dental use and an alloy for baking a porcelain for dental use have been generally cast by the lost wax method. However, a press method which is conventionally used for preparing a glass ceramic has been also used, in recent year. Phosphate-based investment material have been used for casting metals having high melting point conventionally. In recent year, the phosphate-based investment material has been used for casting metals having high melting point and metals having low melting point and used as an investment material for pressing a press ceramic.

The composition of the phosphate-based investment material consists of a powder material and a liquid material which are kneaded and hardened for use. The powder material contains magnesium oxide and ammonium dihydrogen phosphate as a binder, and silica, alumina, zircon and the like as a refractory material (aggregate). The liquid material contains an aqueous solution including colloidal silica, which is a dedicated liquid.

One of advantage of this investment material is that the total expansion corresponding to the cast shrinkage of various metals can be obtained by adjusting the concentration of colloidal silica of the dedicated liquid. Therefore, this investment material can be widely used, for example, for press ceramics, for precious alloys mainly composed of gold, and for non-precious alloys mainly composed of nickel and/or cobalt.

In order to compensate for the cast shrinkage of the non-precious alloy, the total expansion of 2.5% or more is required. In ordinary phosphate-based investment material, it is difficult to obtain the thermal expansion amount of 1.5% or more. Therefore, it is necessary to obtain the hardening expansion from the dedicated liquid. In the ordinary methods, in addition to adjustment of thermal expansion amount of the phosphate-based investment material based on the component other than the dedicated liquid, the dedicated liquid is adjusted such that the hardening expansion is 1.5% or more when kneading with only the dedicated liquid. This adjusted dedicated liquid is diluted according to the expansion/shrinkage amount of the metal for use.

The press ceramics have been roughly divided into two kinds of forms in dental use. That is, there are a press ceramic reinforced with a leucite crystal and a press ceramic reinforced with lithium disilicate crystal, in order to enhance the strengh. Although the leucite-reinforcement type press ceramic generally has the bending strength of about 100 to 200 MPa, this bending strength is insufficient for the prosthesis restoration of the dental crown bridge. Recently, press ceramics having a crystal form called as lithium disilicate have been applied in a dental field. In these press ceramics, a crystal of $Li_2Si_2O_5$ is deposited from the glass composition containing $SiO_2$, $Li_2O$ and $Al_2O_3$ as a base components, and the bending strength is generally from 400 to 500 MPa. The molding temperature of this ingot is often around 900° C., and therefore a phosphate-based investment material has been used in dental use. However, there is a problem in which a reaction layer is generated between a pressed-molded body (press ceramic) and an investment material when the ingot is pressed. This reaction layer is generated by contacting of a molded body of an ingot (press ceramic) with an investment material at high temperature in pressing the ingot into the investment material after softening of the ingot. Generally, a blast-treatment by alumina particles or an acid treatment by fluorinated acid is applied to the reaction layer. Thereafter, a dental dedicated colorant called the stain is generally applied to imitate a tooth crown color. However, in the case that the reaction layer is thick, there is a problem that the compatibility with the mold model is deteriorated.

An aqueous solution including a colloidal silica, which is a liquid material of a phosphate-based investment material, is cured by kneading with a powder material. In curing, the value of the hardening expansion changes according to the particle diameter and the concentration of the colloidal silica. Furthermore, in lost-wax method, because the investment material is used after raising a temperature to 800-900° C., the thermal expansion occurs. The solidification shrinkage and the thermal shrinkage of the metal and the press-ceramic are supplemented by the total value of the hardening expansion and the thermal expansion and thereby adjust the compatibility of the prosthetic device.

On the other hand, most aqueous solutions including a colloidal silica used as a liquid material of a phosphate-based investment material are alkaline and aqueous solutions having the pH value of 8 to 11 are used, generally. The curing time of the investment material may be adjusted by varying the pH value. The colloidal silica consists of an amorphous component of $SiO_2$, and the colloidal silica having the average particle diameter of 4 to 100 nm is generally used.

Japanese Unexamined Patent Application Publication No. 2003-34608 discloses a rapid heating-type phosphate-based investment material for casting. More specifically, a technique to impart lubricity to the surface of the casting body by defining the particle size of a binding material of the phosphate-based investment material is disclosed. However, although the lubricity is imparted to the surface of the metal casting body, this technique is insufficient to impart the lubricity to the surface of a press ceramic such as lithium disilicate.

Japanese Unexamined Patent Application Publication No. 2003-220446 discloses a kneading liquid of a phosphate-based investment material. More specifically, a technique for adjusting a kneading liquid including an alkali metal salt and acid salt into an acidic region to enable charging a cast mold into a furnace is disclosed. However, because the colloidal silica component is not included basically, the hardening expansion was insufficient and the performance was insufficient for an investment material for press ceramic.

International Publication No. WO 2016/117395 discloses an investment material for a press ceramic containing a heat-resistant pigment. The investment material in this technique may be easily identified when a press-ceramic molded body is dug out. However this technique is also insufficient to impart the lubricity to the surface of a press ceramic.

International Publication No. WO 2016/084585 discloses a mold release material for a wax pattern used in press ceramic molding. Although the mold-releasing effect between the press ceramic and the investment material is improved, this technique is also insufficient to impart the lubricity to the surface of a press ceramic.

SUMMARY OF THE INVENTION

Technical Problem

The present disclosure provides a phosphate-based dental investment material which can be used for a metal and a press ceramic and especially can impart the lubricity to the surface of a press ceramic. Further, the present disclosure provides a phosphate-based dental investment material which can be subjected to a rapid heating for using a press ceramic, can obtain a sufficient hardening expansion, and can be easily removed after press molding.

Solution to Problem

The present inventors have made intensive studies in order to solve the above problem, and as a result, have found the present invention.

The present disclosure provides a phosphate-based dental investment material comprising a powder material and a liquid material, wherein
the powder material contains
(a) magnesium oxide: 5 to 20 wt. %;
(b) ammonium dihydrogenphosphate: 8 to 25 wt. % and
the liquid material contains
(c) aqueous solution including a cation-treated colloidal silica.

In a phosphate-based dental investment material of the present disclosure, it is preferable that the content of alkali metals (the content of alkali metal oxide) in the (c) aqueous solution including cation-treated colloidal silica is in a range of 0.001 to 0.30 wt. %.

In a phosphate-based dental investment material of the present disclosure, it is preferable that the pH value of the (c) aqueous solution including cation-treated colloidal silica is in a range of 8.0 to 10.0.

In a phosphate-based dental investment material of the present disclosure, it is preferable that the cation-treatment is an alumina compound treatment.

Advantageous Effects of Invention

The present disclosure provides a phosphate-based dental investment material which can suppress a seizure of the molded body after pressing, impart the lubricity to the surface of a press ceramic and improve the compatibility of the prosthetic device. In addition, the present disclosure provides a phosphate-based dental investment material in which the kneadability is excellent, the curing time of the investment material can set appropriately, and a crack-peeling does not generate even if it is rapidly heated. These effects are especially exhibited in a press process of lithium disilicate glass ceramic.

DETAILED DESCRIPTION OF THE PREFERRED EMBODIMENTS

A phosphate-based dental investment material according to the present disclosure will be described below. However, the present disclosure is not limited to following description.

A phosphate-based dental investment material of the present disclosure consists of a powder material and a liquid material.

The powder material contains (a) magnesium oxide and (b) ammonium dihydrogen phosphate.

The type of the (a) magnesium oxide contained in the powder material is not particularly limited, but it is preferable that the purity of the (a) magnesium oxide is high and it is preferable that the (a) magnesium oxide is finely pulverized.

An average particle diameter of the (a) magnesium oxide is not particularly limited, but the average particle diameter is preferably within a range of 15 to 40 µm, more preferably within a range of 20 to 30 µm. In the particle size distribution of the magnesium oxide, it is preferable that a ratio of particle having 100 µm or more of a particle diameter is 1% or less, and it is more preferable that no particles having 100 µm or more of a particle diameter are contained. Further, a combination of a plurality of the (a) magnesium oxides which have different average particle diameters can be used. In the case of using a combination of a plurality of the (a) magnesium oxides which have different average particle diameters, it is preferable that an average particle diameter of the (a) magnesium oxides after combination is within a range of 15 to 40 µm.

In order to exhibit the effect of the present disclosure in the phosphate-based dental investment material of the present disclosure, a compounded amount of the magnesium oxide must be within a range of 5 to 20 wt. % based on the powder material of the phosphate-based dental investment material. When the compounded amount of the magnesium oxide is less than 5 wt. %, because the sufficient strength of mold is not provided, it may be insufficient for mold material. When the compounded amount of the magnesium oxide is more than 20 wt. %, because the compounded amount of an aggregate becomes less, enough thermal expansion may be not provided.

The (b) ammonium dihydrogen phosphate contained in the powder material constituting the phosphate-based dental investment material of the present disclosure is not particularly limited as long as it is soluble, and any ammonium dihydrogen phosphate can be used without any problem even if having any average particle diameter and any shape.

However, in order to act as a binding material in an investment material, it is preferable that the maximum particle diameter of the ammonium dihydrogen phosphate is small. For maintaining the lubricative property of the surface of the molded body which is press-molded, it is preferable that no particle having a particle diameter of 60 µm or more are contained. Further, a ratio of particles having a particle diameter of 25 µm or less in the particles having a particle diameter of 60 µm or more is preferably within a range of 10 to 45%, more preferably within a range of 20 to 35%.

In order to exhibit the effect of the present disclosure in the phosphate-based dental investment material of the present disclosure, a compounded amount of the ammonium dihydrogen phosphate must be within a range of 8 to 25 wt. % based on the powder material of the phosphate-based dental investment material. When the compounded amount of the ammonium dihydrogen phosphate is less than 8 wt. %, because the sufficient strength of the cast mold is not provided, it may be insufficient for a mold material. When the compounded amount of the ammonium dihydrogen phosphate is more than 25 wt. %, a problem such that the surface property of a casting body or a pressed body becomes rough may be caused.

With respect to a compounding ratio of the (a) magnesium oxide and the (b) ammonium dihydrogenphosphate which are contained in the powder material constituting the phosphate-based dental investment material of the present disclosure, the weight ratio of (a)/(b) is preferably within a range of 0.3 to 1.0 and is more preferably within a range of 0.4 to 0.8.

The powder material constituting the phosphate-based dental investment material of the present disclosure may include an aggregate. Any refractory materials used in a dental casting investment material can be used as an aggregate without any limitation. Specific examples of an aggregate include quartz, cristobalite, fused quartz, alumina, zirconia, zirconium silicate, calcia and yttoria. Among them, zirconia, zirconium silicate, quartz and cristobalite are especially preferable. In order to adjust the fluidity of the investment material, a combination of a plurality of the aggregates which have average particle diameters within a range of 10 to 300 µm can be used.

In order to exhibit the effect of the present disclosure in the phosphate-based dental investment material of the present disclosure, a compounded amount of an aggregate is not particularly limited. However, in the case of using for a press ceramic, the compounded amount of cristobalite is desirably small, preferably within a range of 15 to 45 wt. % and more preferably within a range of 25 to 35 wt. %. On the other hand, the compounded amount of zirconia is preferably within a range of 5 to 10 wt. % and the compounded amount of zirconium silicate is preferably within a range of 5 to 15 wt. %.

Next, the (c) aqueous solution including a cation-treated colloidal silica contained in the liquid material constituting the phosphate-based dental investment material of the present disclosure is described. In order to exhibit the effect of the present disclosure, it is essential that the surface of the colloidal silica is cation-treated. The methods of cation treatment are roughly divided into two kinds of methods including a treatment method using a cationic silane coupling material and a treatment method using a cationic metal element. A water-soluble metal salt may be included in addition to the colloidal silica. Specific examples include sodium chloride.

The preparation methods of a colloidal silica are roughly divided into two methods. That is, two methods including a water glass method and an alkoxide method have been used mainly.

In the water glass method, a sodium silicate is subjected to an ion exchange to prepare an active silicic acid, and the pH value is adjusted with NaOH under heating.

The alkoxide method, otherwise known as the Stöber method, comprises subjecting an alkyl silicate (tetraalkoxysilane) to hydrolyzation and condensation in the presence of a basic catalyst to grow particles, thereby producing silica particles. This method enables the preparation of colloidal particles having particle sizes ranging from nano- to microscale. For example, a colloidal silica having a minor axis diameter of 10 to 200 nm and a major-axis/minor-axis ratio of 1.4 to 2.2 may be prepared by dropping a methyl silicate (tetramethoxysilane) or a mixture of methyl silicate and methanol dropwise to a mixed solvent comprising water, methanol and ammonia, or to a mixed solvent comprising ammonia and ammonium salt under stirring for 10 to 40 minutes so as to allow the methyl silicate to react with water.

When a cationic colloidal silica is prepared from a colloidal silica by using a silane coupling material, an aqueous solution including a colloidal silica is prepared in advance by the water glass method or the alkoxide method and then the colloidal silica is surface-treated with a silane coupling material. In addition, a commercially available aqueous solution including a colloidal silica may be used without any problem. In this case, a solid content concentration of an aqueous solution including a colloidal silica suitable for the present disclosure preferably is preferably within a range of 15 to 40 wt. %, more preferably within a range of 20 to 30 wt. %. Further, the primary particle diameter of this colloidal silica is not particularly limited, but is preferably within a range of 5 to 30 nm, and more preferably within a range of 8 to 20 nm.

For a method for preparing an aqueous solution including a cationic colloidal silica by using a silane coupling material, there is a method to treat a colloidal silica by adding the treated amount of a silane coupling material to a colloidal silica aqueous solution and stirring. In addition, for example, a desired treatment liquid can be prepared by heating to 50 to 80° C. and stirring for 1 to 2 hours. It is preferable that the weight ratio of a colloidal silica aqueous solution and a silane coupling material is within a range of 50:1 to 5:1.

Specific examples of the silane coupling material include N-(ß-aminoethyl)-γ-aminopropyl methyldimethoxysilane, N-(ß-aminoethyl)-γ-aminopropyl trimethoxysilane, N-(ß-aminoethyl)-γ-aminopropyl triethoxysilane, γ-aminopropyltriethoxysilane, γ-aminopropyltrimethoxysilane, γ-triethoxysilyl-N-(α, γ-dimethyl-butylidene) propylamine, N-phenyl-γ-aminopropyltrimethoxysilane, hydrochloride of N-(vinylbenzyl)-ß-aminoethyl-γ-aminopropyl triethoxysilane and octadecyl dimethyl(γ-trimethoxysilylpropyl)ammonium chloride.

Among them, N-(ß-aminoethyl)-γ-aminopropyl trimethoxysilane, N-(ß-aminoethyl)-γ-aminopropyl triethoxysilane, γ-aminopropyltriethoxysilane, γ-aminopropyltriethoxysilane and γ-aminopropyltrimethoxysilane are preferably used because of good reactivity to colloidal silica.

These silane coupling materials can be used singly or in combinations of a plurality thereof.

It is preferable that the pH value is adjusted to 8-10 by adding an alkali metal compound after a silane coupling treatment.

Sodium hydroxide and potassium hydroxide are suitably used as an alkali metal compound.

The other cation treatment method of a colloidal silica is a method for treating the surface with a metallic element. In this method, a metal compound is mixed in advance during a preparation of colloidal silica by the water glass method, an active silicic acid is prepared by an ion change of a sodium silicate and the pH value is adjusted by adding NaOH under heating. Specific examples of the metal compound include an alumina compound, a titanium compound, a zirconia compound or the like and a colloidal silica having a surface coated with these metal compounds can be used. The coating method is not particularly limited and a mixing reaction method in an aqueous solution can be used. An alumina compound treatment is particularly preferable.

Specifically, sodium aluminate, sodium titanate, sodium zirconate or the like is added to a colloidal silica aqueous solution, and then heated and stirred to prepare a cation-treated colloidal silica.

Sodium hydroxide and potassium hydroxide are suitably used as an alkali metal compound. In addition, the pH value is adjusted to 8-10 by adding an alkali metal compound.

In this case, a solid content concentration of a cationic colloidal silica treated with a metal element is preferably within a range of 15 to 40 wt. %, more preferably within a range of 20 to 30 wt. %. Further, the primary particle diameter of this colloidal silica is not particularly limited, but is preferably within a range of 5 to 30 nm, and more preferably within a range of 8 to 20 nm.

It is preferable that the (c) aqueous solution including a cation-treated colloidal silica contains an alkali metal, it is more preferable that the content of alkali metals (in terms of oxide) is 0.30 wt. % or less. Further, it is more preferable that the content of alkali metals (in terms of oxide) is 0.001 wt. % or more.

When the content of alkali metals (in terms of oxide) is less than 0.001 wt. %, a problem of extreme elongation of the curing time of an investment material may occur. Further, when the content of alkali metals (in terms of oxide) is more than 0.30 wt. %, a problem of the surface roughness of a pressed-molded body may occur.

Further, it is preferable that the pH value of the (c) aqueous solution including a cation-treated colloidal silica is within a range of 8.0 to 10.0. When the pH value is less than 8.0, a problem of extreme elongation of the curing time of an investment material may occur. When the pH value is more than 10.0, a problem of shortening of the curing time of an investment material may occur.

With respect to a kneading ratio of the powder material and the liquid material in the phosphate-based dental investment material of the present disclosure, it is preferable that 17 to 25 ml, more preferably 18 to 22 ml of the liquid material, is kneaded with 100 g of the powder material.

Hereinafter, the present disclosure is described by way of Examples in more detail, and specifically, but the present disclosure is not limited to these Examples.

Examples

Hereinafter, the present disclosure is described by way of Examples in more detail, and specifically, but the present disclosure is not limited to these Examples. In the Examples, "Microtrac HRA type" (manufactured by Nikkiso Co., Ltd.) was used for measuring the particle size, and JIS standard sieve was used for sieving ammonium dihydrogenphosphate.

[Powder Material]
(Preparation of Magnesium Oxide Material)

Magnesium oxide raw material was crushed and classified to prepare a magnesium oxide material in which the the average particle diameter is 25 μm and the ratio of the particles having the particle diameter of 100 μm or more is 1% or less.

(Preparation of Ammonium Dihydrogenphosphate Material)

Ammonium dihydrogenphosphate was crushed and adjusted so that the particles have diameters which can pass through a 250-mesh screen (60 μm) and the ratio of particles which can pass through a 500-mesh screen (25 μm) is 30 wt. % to prepare ammonium dihydrogenphosphate material.

(Aggregate)

Cristobalite (200-mesh screen (77 μm) through), quartz (200-mesh screen (77 μm) through), zirconium silicate (200-mesh screen (77 μm) through), and zirconia (200-mesh screen (77 μm) through) are used as the aggregate.

The powder materials are prepared by mixing the compositions shown in following Example of the Table using a ball mill for 30 minutes, and classified with a sieve of 1,000 μm.

(Preparation of Liquid Material A)

An acidic colloidal silica having the primary particle diameter of 10 nm (30% of the solid content concentration) was added with N-(ß-aminoethyl)-γ-amino propyl trimethoxy silane (manufactured by Shinetsu Chemical Co., Ltd.: KBM-603) at the mass ratio of 10:1, and heated to 80° C. and stirred. Thereafter, the pH value was adjusted to 9 by adding 1N of a sodium hydroxide solution. The content of alkali metals (in terms of oxide) is 0.10 wt. %.

(Preparation of Liquid Material B)

Liquid material B was prepared by performing the same treatment as that of the Liquid material A and adjusting the pH value to be 7. In the Liquid material B, the content of alkali metals (in terms of oxide) is 0.01 wt. %.

(Preparation of Liquid Material C)

Liquid material C was prepared by performing the same treatment as that of the Liquid material A and adjusting the pH value to be 11. In the Liquid material C, the content of alkali metals (in terms of oxide) is 0.60 wt. %.

(Preparation of Liquid Material D)

Liquid material D was prepared by performing the same treatment as that of the Liquid material A and adjusting the pH value to be 8. In the Liquid material D, the content of alkali metals (in terms of oxide) is 0.01 wt. %.

(Preparation of Liquid Material E)

Liquid material E was prepared by performing the same treatment as that of the Liquid material A and adjusting the pH value to be 10. In the Liquid material E, the content of alkali metals (in terms of oxide) is 0.20 wt. %.

(Preparation of Liquid Material F)

A raw material was prepared by adding sodium aluminate to commercially available sodium silicate aqueous solution which is a base material and then the raw material was warmed/heated to prepare a colloidal silica aqueous solution. In this colloidal silica aqueous solution, the molar ratio of $Al_2O_3/SiO_2$ was adjusted to 0.001. In this colloidal silica aqueous solution, the primary particle diameter is adjusted to 10 nm by controlling the particle diameter of the silica in a concentration process of the ion exchange, the solid content concentration is adjusted to 30% and the pH value is adjusted to 9 by adding an alkali metal. The content of alkali metals (in terms of oxide) is 0.1 wt. %.

(Preparation of Liquid Material G)

Liquid material G was prepared by performing the same almina treatment as that of the Liquid material F using the colloidal silica used in the Liquid material F and adjusting the pH value to be 7. In the Liquid material G, the content of alkali metals (in terms of oxide) is 0.02 wt. %.

(Preparation of Liquid Material H)

Liquid material H was prepared by performing the same almina treatment as that of the Liquid material F using the colloidal silica used in the Liquid material F and adjusting the pH value to be 12. In the Liquid material H, the content of alkali metals (in terms of oxide) is 0.80 wt. %.

(Preparation of Liquid Material I)

Liquid material I was prepared by performing the same alumina treatment as that of the Liquid material F using the colloidal silica used in the Liquid material F and adjusting the pH value to be 8. In the Liquid material I, the content of alkali metals (in terms of oxide) is 0.01 wt. %.

(Preparation of Liquid Material J)

Liquid material J was prepared by performing the same almina treatment as that of the Liquid material F using the colloidal silica used in the Liquid material F and adjusting the pH value to be 10. In the Liquid material J, the content of alkali metals (in terms of oxide) is 0.20 wt. %.

(Preparation of Liquid Material K (Colloidal Silica Aqueous Solution for the Comparative Example))

In the Comparative Examples, an aqueous solution including a colloidal silica which was not cation-treated (manufactured by JGC Catalysts and Chemicals Ltd: SI-30) was used. The primary particle diameter is 11 nm and the solid content concentration is 30%. This aqueous solution was used as Liquid material K.

(Measurements of Initial Curing Time, Compression Strength and Crack-Peeling Test)

Investment materials were prepared by using the powder materials and the liquid materials according to the composition list of following Examples and Comparative Examples. The prepared investment materials were performed with Initial Curing time, Compression strength and Crack-peeling test according to JIS T 6608:2001 (Phosphate-based dental investment material). Because the present disclosure relates to an investment material for pressing, Crack-peeling test was performed in ringless state. The rating criteria of Crack-peeling test were as follow: ○: no crack-peeling; Δ: there is slight crack, but there is no hindrance in pressing; and x: there is a crack which makes performing the pressing impossible.

(Evaluation of Reaction Layer)

Wax plates having a dimension of 10 mm by 10 mm by 1 mm (thickness) were prepared and planted on a ring base for pressing.

The investment materials prepared by using the powder materials and the liquid materials according to the composition list of following Examples and Comparative Examples were kneaded by a laboratory mixer (manufactured by SHOFU INC.) for 60 seconds and injected into a ring for pressing. After 20 minutes from the inventiment, they were thrown into a furnace of 850° C. to hold for 1 hour. Thereafter, a lithium disilicate ingot "vintage LD" (manufactured by SHOFU INC.) was pressed according to the press schedule described in the instruction book. After finishing the press, the moded body was dug out and the existence of the reaction layer was visually evaluated. The surface attached with the reaction layer was scanned by the three dimensional laser microscope and the area of the reaction layer was calculated. The case that the surface of the molded body has no reaction layer is defined as 100% of score and the case that the reaction layer is attached to the entire surface of the molded body is defined as 0% of score. Based on these definition, the ratio of the area of the reaction layer to the the surface of the molded body was evaluated.

TABLE 1

|  |  |  | Example 1 | Example 2 | Example 3 | Example 4 |
|---|---|---|---|---|---|---|
| Powder Material | Aggregate compounded amount [wt. %] | Cristobalite | 30 | 30 | 25 | 25 |
|  |  | Quartz | 40 | 40 | 35 | 35 |
|  |  | zirconium silicate | 5 | 5 | 5 | 5 |
|  |  | zirconia | 5 | 5 | 5 | 5 |
|  | Binding material compounded amount [wt. %] | Magnesium oxide | 6 | 6 | 10 | 10 |
|  |  | Ammonium dihydrogenphosphate | 14 | 14 | 20 | 20 |
| Liquid material | Type of liquid material |  | A | F | A | F |
|  | Mixing ratio of Liquid material (Quantity of Liquid material per 100 g of Powder material [mL] |  | 20 | 20 | 20 | 20 |
|  | Initial Curing time [Min] |  | 9.0 | 9.0 | 10.0 | 10.0 |
|  | Compression strength [MPa] |  | 15.3 | 14.3 | 18.3 | 17.4 |
|  | Crack-peeling test |  | ○ | ○ | ○ | ○ |
|  | Evaluation of Reaction layer of press-molded body |  | 66 | 75 | 52 | 78 |

TABLE 2

|  |  |  | Example 5 | Example 6 | Example 7 | Example 8 |
|---|---|---|---|---|---|---|
| Powder Material | Aggregate compounded amount [wt. %] | Cristobalite | 30 | 30 | 30 | 30 |
|  |  | Quartz | 40 | 40 | 40 | 40 |
|  |  | zirconium silicate | 5 | 5 | 5 | 5 |
|  |  | zirconia | 5 | 5 | 5 | 5 |
|  | Binding material compounded amount [wt. %] | Magnesium oxide | 6 | 6 | 6 | 6 |
|  |  | Ammonium dihydrogenphosphate | 14 | 14 | 14 | 14 |
| Liquid material | Type of liquid material |  | B | C | G | H |

TABLE 2-continued

|  | Example 5 | Example 6 | Example 7 | Example 8 |
|---|---|---|---|---|
| Mixing ratio of Liquid material (Quantity of Liquid material per 100 g of Powder material [mL] | 18 | 22 | 18 | 22 |
| Initial Curing time [Min] | 13.0 | 5.0 | 14.0 | 5.0 |
| Compression strength [MPa] | 9.5 | 10.1 | 12.1 | 12.8 |
| Crack-peeling test | Δ | ◯ | Δ | ◯ |
| Evaluation of Reaction layer of press-molded body | 66 | 55 | 62 | 58 |

TABLE 3

|  |  |  | Example 9 | Example 10 | Example 11 | Example 12 |
|---|---|---|---|---|---|---|
| Powder Material | Aggregate compounded amount [wt. %] | Cristobalite | 30 | 30 | 30 | 30 |
|  |  | Quartz | 40 | 40 | 40 | 40 |
|  |  | zirconium silicate | 5 | 5 | 5 | 5 |
|  |  | zirconia | 5 | 5 | 5 | 5 |
|  | Binding material compounded amount [wt. %] | Magnesium oxide | 6 | 6 | 6 | 6 |
|  |  | Ammonium dihydrogenphosphate | 14 | 14 | 14 | 14 |
| Liquid material | Type of liquid material |  | D | E | I | J |
|  | Mixing ratio of Liquid material (Quantity of Liquid material per 100 g of Powder material [mL] |  | 20 | 20 | 20 | 20 |
|  | Initial Curing time [Min] |  | 9.0 | 7.0 | 9.0 | 7.0 |
|  | Compression strength [MPa] |  | 9.0 | 10.5 | 8.6 | 10.5 |
|  | Crack-peeling test |  | Δ | ◯ | Δ | ◯ |
|  | Evaluation of Reaction layer of press-molded body |  | 66 | 65 | 75 | 70 |

TABLE 4

|  |  |  | Example 13 | Example 14 | Example 15 |
|---|---|---|---|---|---|
| Powder Material | Aggregate compounded amount [wt. %] | Cristobalite | 30 | 30 | 30 |
|  |  | Quartz | 26 | 46 | 29 |
|  |  | zirconium silicate | 5 | 5 | 5 |
|  |  | zirconia | 5 | 5 | 5 |
|  | Binding material compounded amount [wt. %] | Magnesium oxide | 20 | 6 | 6 |
|  |  | Ammonium dihydrogenphosphate | 14 | 8 | 25 |
| Liquid material | Type of liquid material |  | A | A | A |
|  | Mixing ratio of Liquid material (Quantity of Liquid material per 100 g of Powder material [mL] |  | 20 | 20 | 20 |
|  | Initial Curing time [Min] |  | 6.0 | 12.0 | 13.0 |
|  | Compression strength [MPa] |  | 10.1 | 9.6 | 11.0 |
|  | Crack-peeling test |  | ◯ | Δ | Δ |
|  | Evaluation of Reaction layer of press-molded body |  | 81 | 95 | 61 |

TABLE 5

|  |  |  | Comparative Example 1 | Comparative Example 2 | Comparative Example 3 | Comparative Example 4 |
|---|---|---|---|---|---|---|
| Powder Material | Aggregate compounded amount | Cristobalite | 30 | 25 | 30 | 30 |
|  |  | Quartz | 40 | 35 | 42 | 24 |
|  |  | zirconium silicate | 5 | 5 | 5 | 5 |

TABLE 5-continued

| | | | Comparative Example 1 | Comparative Example 2 | Comparative Example 3 | Comparative Example 4 |
|---|---|---|---|---|---|---|
| | [wt. %] | zirconia | 5 | 5 | 5 | 5 |
| | Binding material compounded amount [wt. %] | Magnesium oxide | 6 | 10 | 4 | 22 |
| | | Ammonium dihydrogenphosphate | 14 | 20 | 14 | 14 |
| Liquid material | Type of liquid material | | K | K | F | F |
| | Mixing ratio of Liquid material (Quantity of Liquid material per 100 g of Powder material [mL] | | 20 | 20 | 20 | 20 |
| | Initial Curing time [Min] | | 8 | 8 | 16 | 4 |
| | Compression strength [MPa] | | 15.7 | 16.9 | 5.6 | 16.2 |
| | Crack-peeling test | | ○ | ○ | X | X |
| | Evaluation of Reaction layer of press-molded body | | 22 | 9 | Impossible to press | Impossible to press |

TABLE 6

| | | | Comparative Example 5 | Comparative Example 6 |
|---|---|---|---|---|
| Powder Material compounded amount [wt. %] | Aggregate | Cristobalite | 30 | 30 |
| | | Quartz | 48 | 26 |
| | | zirconium silicate | 5 | 5 |
| | | zirconia | 5 | 5 |
| | Binding material compounded amount [wt. %] | Magnesium oxide | 6 | 6 |
| | | Ammonium dihydrogen-phosphate | 6 | 28 |
| Liquid material | Type of liquid material | | K | K |
| Mixing ratio of Liquid material (Quantity of Liquid material per 100 g of Powder material [mL] | | | 20 | 20 |
| Initial Curing time [Min] | | | 4 | 18 |
| Compression strength [MPa] | | | 4.8 | 10.9 |
| Crack-peeling test | | | x | ○ |
| Evaluation of Reaction layer of press-molded body | | | Impossible to press | 29 |

(Consideration)

In Examples 1 to 15 in which an area of a reaction layer was 50% or less of the surface of a press-molded body, and the scores were 50 or more. In these cases, they can be clinically used without any problem. On the other hand, the score in Comparative example 1 was 22, the score in Comparative example 2 was 9, and the score in Comparative example 6 was 29. The scores in these Comparative examples were very low and therefore a problem for a clinical use may occur. In comparative examples 3-5, it was impossible to perform an evaluation of a reaction layer in a crack-peeling test because of generation of a crack which makes it impossible to press.

[Effect]

As shown in the above result, the present disclosure provides a phosphate-based dental investment material substantially containing no reaction layer even if phosphate-based dental investment material is prepared by press molding a disilicate ingot.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

What is claimed is:

1. A phosphate-based dental investment material comprising a powder material and a liquid material, wherein
   the powder material contains
   (a) magnesium oxide: 5 to 20 wt. %;
   (b) ammonium dihydrogenphosphate: 8 to 25 wt. % and
   the liquid material contains
   (c) aqueous solution including a cation-treated colloidal silica,
   wherein the cation-treated colloidal silica is colloidal silica surface-treated with a cationic silane coupling material or a cationic metal element.

2. The phosphate-based dental investment material according to claim 1, wherein the content of alkali metals (in terms of oxide) in the (c) aqueous solution including cation-treated colloidal silica is in a range of 0.001 to 0.30 wt. %.

3. The phosphate-based dental investment material according to claim 1, wherein the pH of the (c) aqueous solution including cation-treated colloidal silica is in a range of 8.0 to 10.0.

4. A phosphate-based dental investment material comprising a powder material and a liquid material, wherein
   the powder material contains
   (a) magnesium oxide: 5 to 20 wt.%;
   (b) ammonium dihydrogenphosphate: 8 to 25 wt.% and
   the liquid material contains
   (c) aqueous solution including a cation-treated colloidal silica,
   wherein the cation-treatment is alumina compound treatment.

5. The phosphate-based dental investment material according to claim 2, wherein the pH of the (c) aqueous solution including cation-treated colloidal silica is in a range of 8.0 to 10.0.

6. A phosphate-based dental investment material comprising a powder material and a liquid material, wherein
   the powder material contains
   (a) magnesium oxide: 5 to 20 wt.%;
   (b) ammonium dihydrogenphosphate: 8 to 25 wt.% and
   the liquid material contains
   (c) aqueous solution including a cation-treated colloidal silica, wherein the content of alkali metals (in terms of oxide) in the (c) aqueous solution including cation-treated colloidal silica is in a range of 0.001 to 0.30 wt.%, and
wherein the cation-treatment is alumina compound treatment.

7. A phosphate-based dental investment material comprising a powder material and a liquid material, wherein
the powder material contains
(a) magnesium oxide: 5 to 50 wt.%;
(b) ammonium dihydrogenphosphate: 8 to 25 wt.% and
the liquid material contains
(c) aqueous solution including a cation-treated colloidal silica,
wherein the pH of the (c) aqueous solution including cation-treated colloidal silica is in a range of 8.0 to 10.0, and
wherein the cation-treatment is alumina compound treatment.

* * * * *